(12) United States Patent
Bischoff et al.

(10) Patent No.: US 7,921,554 B2
(45) Date of Patent: Apr. 12, 2011

(54) METHOD FOR MANUFACTURING A MEDICAL ELECTRICAL LEAD CONNECTOR RING

(75) Inventors: Thomas C. Bischoff, Minneapolis, MN (US); James M. Iknayan, Andover, MN (US); Paul M. Becker, Cedar, MN (US); Mary L. Cole, St. Paul, MN (US); Jordon D. Honeck, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 600 days.

(21) Appl. No.: 11/945,122

(22) Filed: Nov. 26, 2007

(65) Prior Publication Data

US 2008/0148550 A1 Jun. 26, 2008

Related U.S. Application Data

(62) Division of application No. 11/193,576, filed on Jul. 29, 2005, now abandoned.

(51) Int. Cl.
*H05R 43/04* (2006.01)

(52) U.S. Cl. ........... 29/861; 29/831; 29/882; 219/69.17; 607/116; 439/880; 439/909

(58) Field of Classification Search .......... 128/897–899; 219/69.17; 607/116, 119, 122; 439/880, 439/909; 29/831, 857, 861, 874, 881, 882
See application file for complete search history.

(56) References Cited

U.S. PATENT DOCUMENTS

| | | | |
|---|---|---|---|
| 4,270,825 A | | 6/1981 | Marsh |
| 4,485,287 A | * | 11/1984 | Hamasaki et al. ......... 219/69.17 |
| 4,576,032 A | | 3/1986 | Maack et al. |
| 4,923,416 A | | 5/1990 | Zinn |
| 4,951,687 A | | 8/1990 | Ufford et al. |
| 4,970,350 A | | 11/1990 | Harrington |
| 5,007,435 A | | 4/1991 | Doan et al. |
| 5,385,578 A | | 1/1995 | Bush et al. |
| 5,488,768 A | | 2/1996 | Mar |
| 5,676,694 A | | 10/1997 | Boser et al. |
| 6,026,567 A | | 2/2000 | Swoyer et al. |
| 6,077,227 A | * | 6/2000 | Miesel et al. ................. 128/899 |
| 6,671,553 B1 | | 12/2003 | Helland et al. |
| 7,003,351 B2 | | 2/2006 | Tvaska |
| 7,292,894 B2 | * | 11/2007 | Belden ......................... 607/122 |
| 2004/0064174 A1 | | 4/2004 | Belden |
| 2004/0167582 A1 | | 8/2004 | Tvaska |

FOREIGN PATENT DOCUMENTS

EP 0692843 A2 1/1996

OTHER PUBLICATIONS

International Search Report, PCT/US2006/028604, Oct. 11, 2006, 3 Pages.

\* cited by examiner

*Primary Examiner* — Donghai D. Nguyen
(74) *Attorney, Agent, or Firm* — Carol F. Barry

(57) ABSTRACT

A method of manufacturing a medical electrical device is presented. An inner diameter and an outer diameter of a connector ring is machined to form a first and a second flange extending from the inner diameter. An electric discharge machining wire burner is used to form a conductor channel in the inner diameter of the connector ring. A conductor is positioned within the conductor channel. A first distal end of the first flange is coupled to a second distal end of the second flange.

10 Claims, 4 Drawing Sheets

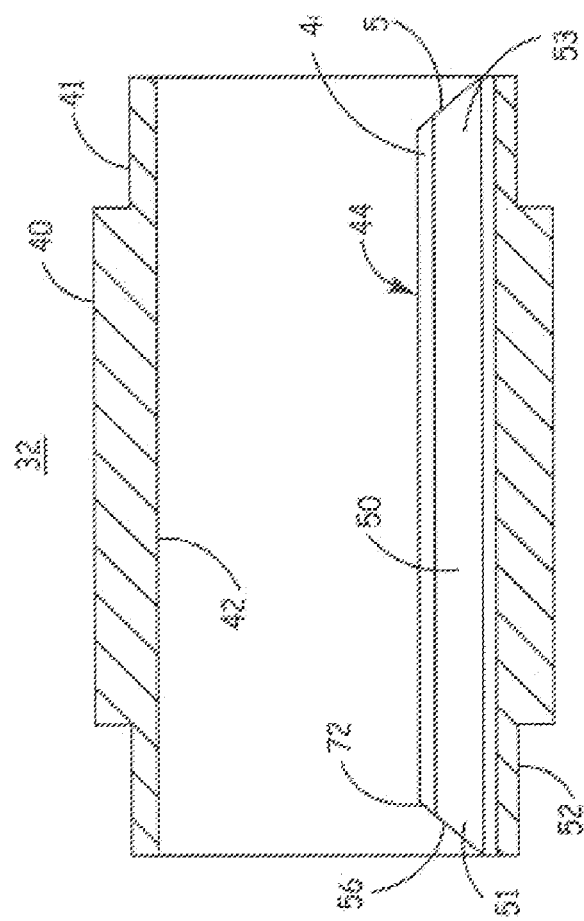
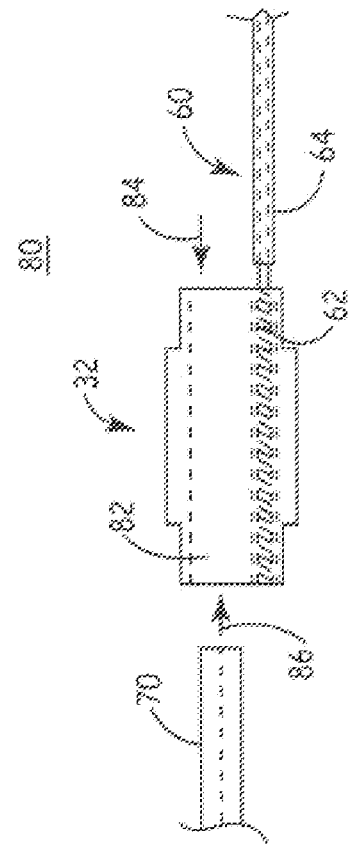
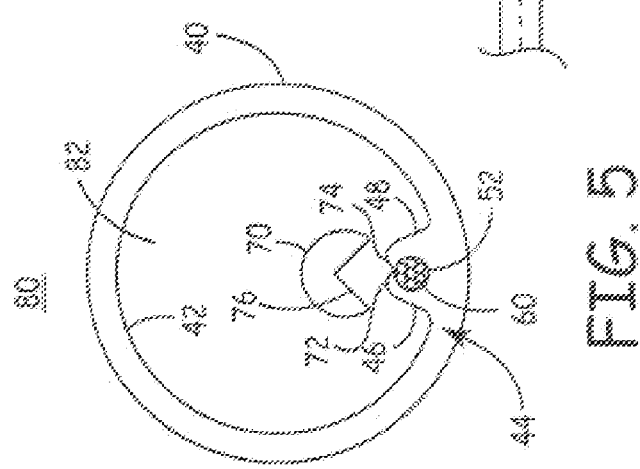

METHOD FOR MANUFACTURING A MEDICAL ELECTRICAL LEAD CONNECTOR RING

CROSS REFERENCE TO PRIORITY APPLICATION

This application is a divisional of application Ser. No. 11/193,576, filed Jul. 29, 2005, now abandoned.

TECHNICAL FIELD

The invention relates to implantable medical devices, and, more particularly, to configurations of implantable medical lead connectors.

BACKGROUND

In the medical field, implantable medical leads are used with a wide variety of therapeutic or monitoring devices. For example, implantable leads are commonly used to form part of implantable cardiac pacemaker systems that provide therapeutic stimulation to the heart by sensing electrical activity of the heart and delivering pacing, cardioversion, or defibrillation pulses via electrodes disposed on the leads, typically near the distal ends of the leads. Electrodes or sensors carried by the lead are generally coupled to a conductor extending to a proximal connector assembly for facilitating electrical coupling of the electrodes or sensors to a therapy delivery or monitoring device. A number of challenges exist with respect to such medical leads. As implantable medical device technology continues to be downsized and more advanced therapeutic techniques are developed, new lead arrangements are required. As such, new configurations for electrically coupling an electrode or other sensor carried by a lead to an associated monitoring or therapy delivery device are needed. In particular, electrical coupling configurations are needed that are reliable and can be manufactured in a cost-effective manner.

BRIEF DESCRIPTION OF THE DRAWINGS

Aspects and features of the present invention will be readily appreciated as the same becomes better understood by reference to the following detailed description when considered in connection with the accompanying drawings, in which like reference numerals designate like parts throughout the figures thereof and wherein:

FIG. 4 is a side cut-away view of a connector ring according to an embodiment of the present invention;

FIG. 5 is an end view of a connector ring according to an embodiment of the present invention;

FIG. 6 is a side view of the connector ring of FIG. 5;

DETAILED DESCRIPTION

The following detailed description provides a practical illustration for implementing various embodiments of the invention and is not intended to limit the scope, applicability, or configuration of the invention in any way.

Figure 1:
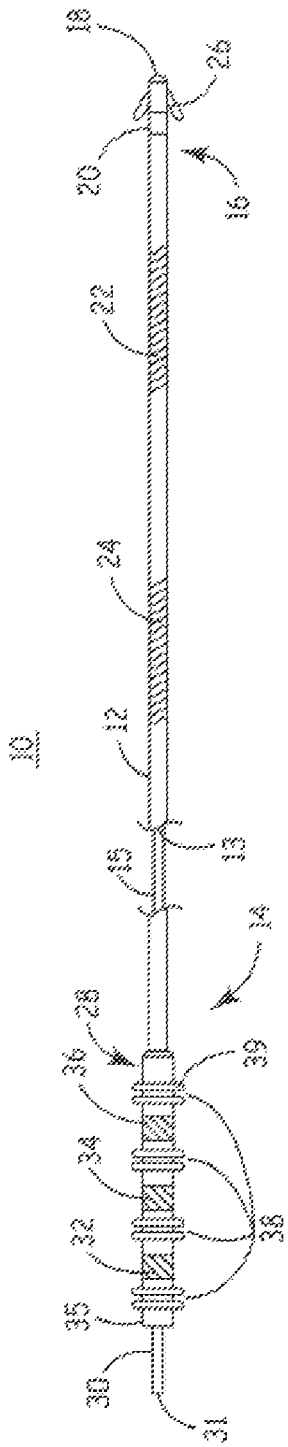
FIG. 1 is a plan view of a medical electrical device according to an embodiment of the present invention.

FIG. 1 is a plan view of a medical electrical device according to an embodiment of the present invention. As illustrated in FIG. 1, a medical electrical device according to an embodiment of the present invention includes a lead 10 embodied as a cardiac pacing lead having electrodes that can be used for sensing cardiac electrogram signals and delivering electrical stimulation pulses to myocardial tissue for pacing, cardioverting or defibrillating the heart. Lead 10 includes an elongated lead body 12 having a proximal end 14 and a distal end 16. Lead 10 is provided with a distal tip electrode 18 located at or near distal end 16 of lead body 12, a ring electrode 20 located proximal to tip electrode 18, and two coil electrodes 22 and 24. Distal tip electrode 18 and ring electrode 20 are commonly used for pacing and sensing the heart. Coil electrodes 22 and 24 are commonly used for delivering high-voltage cardioversion and defibrillation pulses to the heart. While a particular electrode arrangement is shown in FIG. 1, it is recognized that various embodiments of the invention may include a variety of lead types, including neuromuscular stimulation leads, monitoring leads, or any other medical electrical leads. Such leads may be provided with a variety of electrode arrangements, which may include one or more electrodes included on lead body 12. Furthermore, different types of electrodes, such as an active fixation electrode, or any other electrode or sensor known for use with implantable medical leads may be included on lead 10.

Lead body 12 includes at least one lumen 13 through which insulated conductors 15 extend between each of the respective electrodes 18, 20, 22, and 24 and a proximal connector assembly 28 located at proximal body end 14. Connector assembly 28 is adapted for connection to a connector bore included in an associated medical device, such as a pacemaker or neurostimulator device. Such connector assembly configurations for mating with a medical device connector bore are known in the art.

Connector assembly 28 includes a pin connector 30 and three ring connectors 32, 34 and 36. Each of pin connector 30 and ring connectors 32, 34 and 36 are coupled to a respective conductor extending to one of tip electrode 18, ring electrode 20 and coil electrodes 22 and 24 such that each electrode is electrically coupled to one of pin connector 30 or ring connectors 32, 34 and 36 but remain electrically isolated from each other. Upon proper insertion of connector assembly 28 into an associated medical device connector bore, electrodes 18, 20, 22, and 24 become electrically coupled to the medical device circuitry via the respective pin connector 30 and ring connectors 32, 34, and 36 and associated insulated conductors extending between the connectors and the electrodes.

Connector assembly 28 includes an insulative sheath 35 mounted around connector pin 30 and terminating prior to a proximal end 31 of connector pin 30. Connector rings 32, 34, and 36 are mounted on insulative sheath 35 and are thereby insulated from connector pin 30. Connector rings 32, 34 and 36 are insulated from each other by intervening insulative segments 38, which may include sealing rings 39 for forming fluid-tight seals with a corresponding connector bore between each of connector rings 32, 34 and 36. It is recognized that connector assembly 28 may be embodied in a variety of ways, including varying configurations of insulative members for supporting and insulating the required number of connectors needed to electrically couple electrodes or sensors carried by the lead to an associated medical device. Examples of arrangements of a connector pin and one or more connector rings on a connector assembly are generally disclosed in U.S. Pat. No. 4,951,687 issued to Ufford et al., and U.S. Pat. No. 5,007,435 issued to Doan et al.

Figure 2:
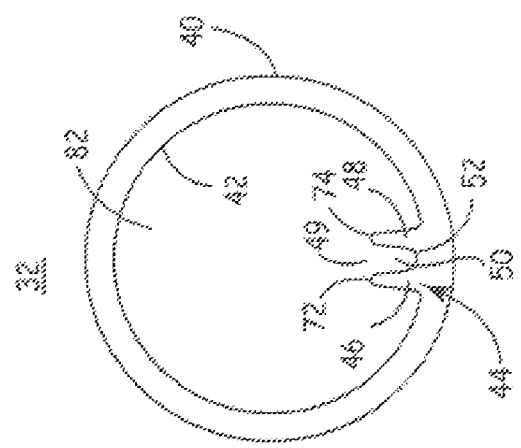
FIG. 2 is an end view of a connector ring according to an embodiment of the present invention included in the medical electrical device of FIG. 1.

FIG. 2 is an end view of a connector ring according to an embodiment of the present invention included in the medical electrical device of FIG. 1. Connector ring 32 is a generally cylindrical member having an outer diameter 40 and inner diameter 42. Connector ring 32 is formed with a conductor channel 44 extending longitudinally along the inner diameter 42 of connector ring 32. Conductor channel 44 is provided for receiving an uninsulated proximal portion of a conductor. The term "channel" as used herein refers to a passage having one open side, such as a generally "U"-shaped or "C"-shaped passage, in contrast to a fully enclosed or annular passage, such as a generally "O"-shaped or "D"-shaped passage. In FIG. 2, conductor channel is shown as a generally "U"-shaped passage formed by two flanges 46 and 48 adapted to be crimped closed around a conductor extending through conductor channel lumen 50. Thus the conductor channel 44 is provided initially as an open passage having open side 49 formed by flanges 46 and 48. The closed side 52 of channel 44 can be formed as a generally curved surface as shown in FIG. 2. Conductor channel lumen 50 is sized to approximately match the outer diameter of a conductor. The proximal portion of the conductor can be positioned in conductor channel 44 by either threading the conductor into conductor channel lumen 50 or by threading the conductor through lumen 82 of connector ring 32 then dropping the conductor down into conductor channel 44 through open side 49.

Connector ring 32 is fabricated from a conductive material, such as MP35N, titanium, or stainless steel. Connector ring 32 is formed during a machining process that includes machining the inner diameter 42 from round stock. In one method, a pilot hole is machined so that an electrical discharge machining wire burner can be threaded through the round stock. The wire burner is then used to form inner diameter 42 and conductor channel 44 in one machining process. The use of electric discharge machining (EDM) wire burner for machining conductor channel 44 reduces the number of machining steps required to machine connector rings as compared to past practice, which used EDM hole popper methods. The EDM wire burner step for forming conductor channel 44 can be performed on multiple, stacked connector ring piece parts to further reduce manufacturing time.

Figure 3:
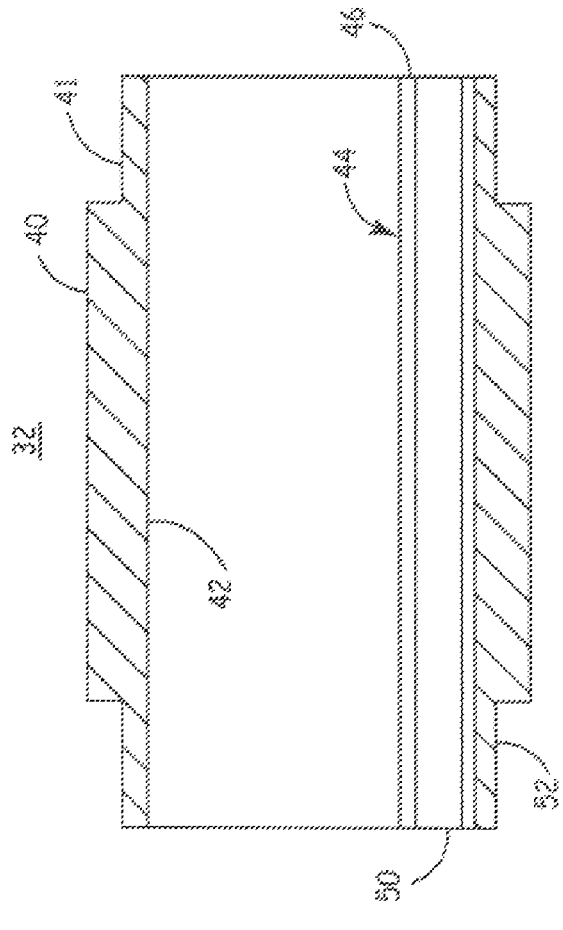
FIG. 3 is a side, cut-away view of a connector ring according to an embodiment of the present invention.

FIG. 3 is a side, cut-away view of a connector ring according to an embodiment of the present invention. Conductor channel 44 is shown extending longitudinally along substantially the entire length of connector ring 32. In alternative embodiments, conductor channel 44 may extend along the inner diameter 42 of connector ring 32 for any portion of the length of connector ring 32. Connector ring 32 may be provided with a contoured outer diameter 41 to accommodate outer insulation sheaths used in assembling a lead connector.

FIG. 4 is a side cut-away view of a connector ring according to an embodiment of the present invention. As illustrated in FIG. 4, according to an embodiment of the present invention, flange 46 of conductor channel 44 may be formed to include chamfered ends 54 and 56. Similarly, flange 48, not seen in the cut away view of FIG. 4, would also be formed to include chamfered ends similar to ends 54 and 56 of flange 46. In a manufacturing process that involves threading the proximal end of a conductor into conductor channel lumen 50, the threading step may be more readily performed when ends 54 and 56 are chamfered since the end openings 51 and 53 to conductor channel lumen 50 will have a larger cross-sectional area than when distal ends of the flanges extend straight up as shown in FIG. 3.

A conductor may be threaded into lumen 50 through either conductor channel end opening 51 or 53. As shown in FIGS. 3 and 4, connector ring 32 provided as a piece part with identically machined ends does not have a designated proximal or distal end. In FIG. 4, flange 46 is provided with chamfered ends 54 and 56 at both end openings 51 and 53. During an assembly process, which may be manual or automated, the connector ring 32 can be oriented in either direction when a conductor is threaded into either end opening 51 or 53 of conductor channel 44. In particular, automated assembly of a conductor onto connector ring 32 is facilitated by providing connector ring 32 with identically machined ends 51 and 53. It is recognized, however, that in other embodiments flanges 46 and 48 can be provided with chamfered ends at only one end opening, 51 or 53. During assembly, the connector ring would need to be properly oriented for a conductor to be threaded into the chamfered end 51 or 53.

FIG. 5 is an end view of a connector ring according to an embodiment of the present invention. As illustrated in FIG. 5, according to an embodiment of the present invention, a connector ring 80 is formed as described above, with a conductor 60 positioned to extend through lumen 50 of conductor channel 44. Conductor 60 is shown as a cable conductor, however, connector ring sub-assembly 80 may be formed using other conductor types, such as a wire, stranded, bundled, or coiled conductor. A crimping tool 70 is pressed down over conductor channel 44 to advance flanges 46 and 48 together such that a distal end 72 of flange 46 is positioned adjacent to or engaged against a distal end 74 of flange 48 to close formerly open side 49 (shown in FIG. 2). Conductor 60 becomes enclosed within conductor channel lumen 50 such that conductor 60 and connector ring 40 are electrically and mechanically coupled.

Crimping tool 70 is an elongated tool that can be inserted through connector ring lumen 82. Crimping tool 70 is provided with a crimping notch 76 that extends along crimping tool 70 for a length corresponding to the length of conductor channel 44. Crimping notch 76 is sized such that when crimping tool 70 is pressed down over conductor channel 44, flanges 46 and 48 will be crimped together within notch 76 along the entire length of conductor channel 44. A mechanical and electrical crimp joint between connector ring 32 and conductor 60 is thereby formed, extending approximately the entire length of conductor channel 44, which has been shown to extend approximately the entire length of connector ring 32. It is expected that by providing a crimp joint extending the entire length of connector ring 32, a reliable mechanical and electrical coupling between connector ring 32 and conductor 60 can be formed which is capable of withstanding a higher tensile force than a crimp joint extending along only a portion of connector ring 32. However, depending on the application, a crimp joint that extends only a portion of the length of connector ring 32 may also provide adequate tensile strength for acceptable lead reliability.

After crimping conductor channel 44 around conductor 60, inspection of the crimp joint is performed. The crimp joint is readily verified by inspecting if distal ends 72 and 74 meet along the entire length of conductor channel 44.

FIG. 6 is a side view of the connector ring of FIG. 5. Crimping tool 70 may be inserted into lumen 82 of connector ring 32 from either end 84 or 86 for crimping conductor channel 44 around conductor 60. The proximal portion of conductor 60 that extends through lumen 50 of conductor channel 44 is stripped of insulation 64. Connector ring 80 can be utilized in manufacturing a medical electrical lead.

Figure 7A:
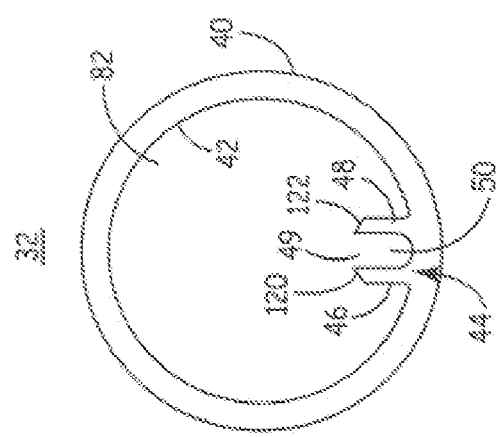
FIG. 7A is an end view of a connector ring according to an embodiment of the present invention.
Figure 7B:
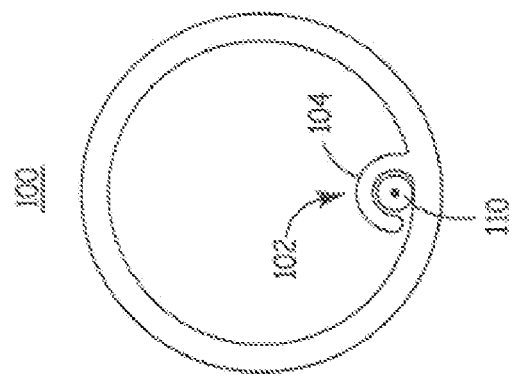
FIG. 7B, is an end view of a connector ring according to an embodiment of the present invention.

FIG. 7A is an end view of a connector ring according to an embodiment of the present invention. As illustrated in FIG. 7A, according to an embodiment of the present invention, a connector ring 100 is provided with a conductor channel 102 having a generally "C"-shaped cross-section with open side 106, and extending along connector ring inner surface 101. A flange 104 forms a conductor channel lumen 108 through which a conductor 110 is threaded. As shown in FIG. 7B, an end 105 of flange 104 is advanced toward inner surface 101 to close open side 106, thereby enclosing conductor 110 within lumen 108 and forming a mechanical and electrical coupling between connector ring 100 and conductor 110.

Figure 8:
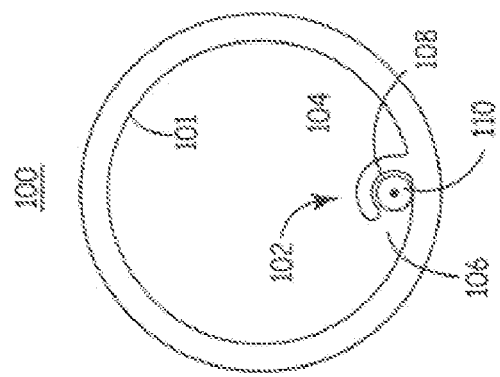
FIG. 8 is an end view of a connector ring of a medical electrical device according to an embodiment of the present invention.

FIG. 8 is an end view of a connector ring of a medical electrical device according to an embodiment of the present invention. Connector ring 32 of the embodiment of FIG. 8 is shown having a generally "U"-shaped conductor channel 44 adapted for crimping around a conductor extending through conductor channel lumen 50. In this embodiment, flanges 46 and 48 are provided with beveled distal ends 120 and 122, respectively. The distal ends 120 and 122 may be provided as rounded, beveled, canted or otherwise modified tips to promote complete and stable closure of open side 49 of conductor channel 44 after crimping. In particular, when connector ring 32 is fabricated from Titanium, beveled distal ends 120 and 122 promote a more reliable crimp joint.

Figure 9:
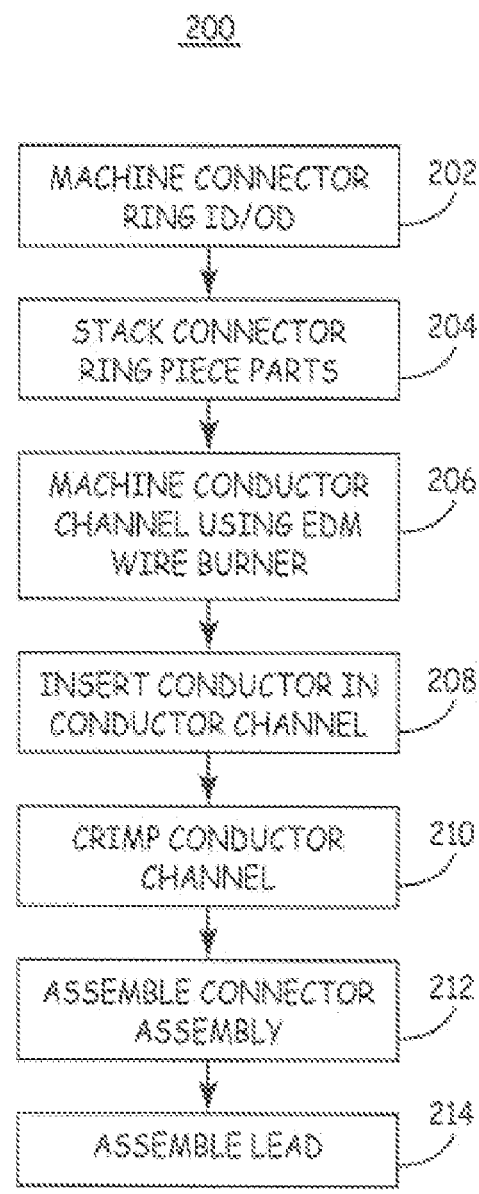
FIG. 9 is a flow chart of a method for manufacturing a medical electrical device according to an embodiment of the present invention.

FIG. 9 is a flow chart of a method for manufacturing a medical electrical device according to an embodiment of the present invention. At step 202, fabrication of a connector ring is initiated, including machining the inner diameter and outer diameter contours of the connector ring from solid, round stock of a selected, conductive metal material. At step 204, partially machined connector rings can be stacked for machining the conductor channel into multiple connector rings simultaneously at subsequent step 206. At step 206, the conductor channel is machined on the inner diameter of the connector ring using an EDM wire burner method.

After completion of connector ring fabrication, a connector ring sub-assembly is assembled. At step 208, a proximal, uninsulated portion of a conductor is inserted through the lumen of the conductor channel. This insertion step may be performed by threading the conductor through an open end of the conductor channel lumen or by threading the conductor through an open end of the connector ring lumen then dropping the conductor down into the conductor channel through the open side of the conductor channel.

After inserting the conductor in the conductor channel, a crimping tool is used to crimp the conductor channel to close the open side of the conductor channel at step 210. The resulting crimp joint formed between the conductor and the conductor channel provides mechanical and electrical coupling between the connector ring and the conductor. The connector ring sub-assembly is then ready to use in assembling a lead connector assembly at step 212. The lead connector assembly can then be used in assembling a medical electrical lead at step 214.

Thus, a connector ring and associated methods for assembling a connector ring sub-assembly, a connector assembly and a medical electrical lead including the connector ring, have been presented in the foregoing description with reference to specific embodiments. It is appreciated that various modifications to the referenced embodiments may be made without departing from the scope of the invention as set forth in the following claims.

What is claimed is:

1. A method of manufacturing a medical electrical device comprising:
   providing a stack of a plurality of connector ring stock piece parts, wherein each of the plurality of connector ring stock piece parts comprises a machined pilot hole such that an electric discharge machining (EDM) wire can be threaded through the connector ring stock piece parts;
   machining the stack to provide an inner diameter of a plurality of connector rings and to form a first and a second flange extending from the inner diameter of each of the plurality of connector rings using the EDM wire, wherein machining the stack to provide the inner diameter further comprises forming a conductor channel in the inner diameter of each of the plurality of connector rings between the first and second flanges, wherein the conductor channel of each of the plurality of connector rings comprises an open side to receive a conductor therein, and further wherein providing the inner diameter, forming the first and second flanges, and forming the conductor channel of the plurality of connector rings is completed in a single machining process;
   positioning a conductor within the conductor channel of at least one of the plurality of connector rings through the open side thereof; and
   moving a first distal end of the first flange to a second distal end of the second flange to couple the at least one connector ring and the conductor.

2. The method according to claim 1, wherein the first distal end of the first flange is crimped to a second distal end of the second flange.

3. The method of claim 1 wherein the first distal end of the first flange contacts the second distal end of the second flange.

4. The method of claim 1 wherein the first distal end of the first flange does not contact the second distal end of the second flange.

5. A method of forming a medical electrical device comprising:
   providing a stack of a plurality of connector ring stock piece parts, wherein each of the plurality of connector ring stock piece parts comprises a machined pilot hole such that an electric discharge machining (EDM) wire can be threaded through the connector ring stock piece parts;
   machining, using the EDM wire, and in a single machining process, an inner surface of a plurality of connector rings to form an inner lumen of each connector ring having at least a first flange extending from the inner surface;
   positioning a conductor within at least one of the plurality of connector rings; and
   advancing a first distal end of the first flange to form a conductor channel to fixedly position the conductor within the at least one connector ring and to electrically couple the connector ring and the conductor.

6. The method of claim 5, further comprising machining, using the EDM wire in the single machining process, at least a second flange extending from the inner surface and advancing a second distal end of the second flange extending from the inner surface to fixedly engage the first distal end and the second distal end to form the conductor channel.

7. The method of claim 5, wherein the first distal end is advanced to be engaged against the inner surface subsequent to the positioning of the conductor within the connector ring.

8. A method of manufacturing a medical electrical device comprising:

providing a stack of a plurality of connector ring stock piece parts, wherein each of the plurality of connector ring stock piece parts comprises a machined pilot hole such that an electric discharge machining (EDM) wire can be threaded through the connector ring stock piece parts;

machining, using the EDM wire in a single machining process, an inner diameter of each of a plurality of connector rings to form at least a first flange extending from the inner diameter of each of the plurality of connector rings and to form a conductor channel in the inner diameter of each of the plurality of connector rings;

positioning a conductor within the conductor channel of at least one of the plurality of connector rings; and advancing a first distal end of at least the first flange towards an inner surface of the connector ring to couple the at least one of the connector rings and the conductor.

9. The method of claim 8 wherein the conductor channel includes a first chamfered end.

10. The method of claim 9 wherein the conductor channel includes a second chamfered end.

* * * * *